Figure 1:
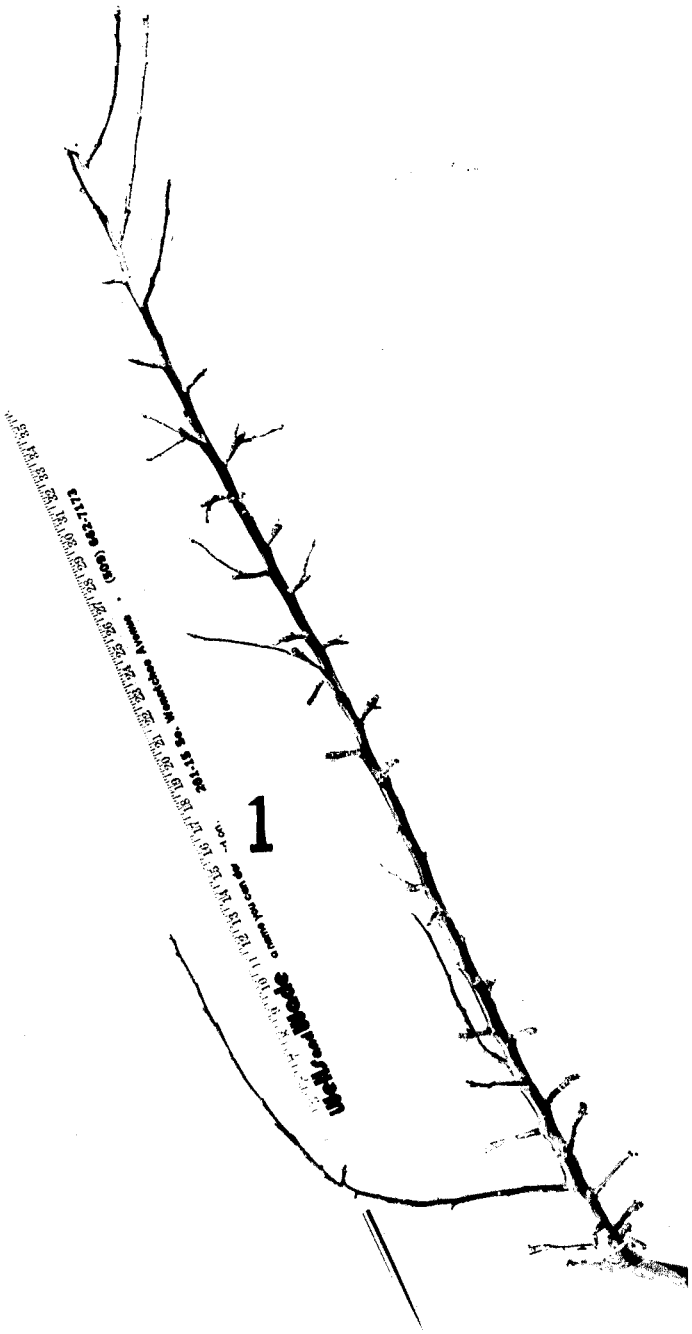

United States Patent [19]

Cooper

[11] Patent Number: Plant 7,363

[45] Date of Patent: Oct. 23, 1990

[54] ROME BEAUTY APPLE—"TIFT SPUR ROME #21"

[75] Inventor: Calvin L. Cooper, Brewster, Wash.

[73] Assignee: Paul G. Tift, Brewster, Wash. ; a part interest

[21] Appl. No.: 200,576

[22] Filed: May 31, 1988

[51] Int. Cl.[5] ..... A01H 5/00

[52] U.S. Cl. ..... Plt./34

[58] Field of Search ..... Plt./34

[56] References Cited

U.S. PATENT DOCUMENTS

| | | | |
|---|---|---|---|
| P.P. 3,121 | 4/1972 | Taylor | Plt. 34 |
| P.P. 3,198 | 5/1972 | Miller | Plt. 34 |
| P.P. 4,096 | 8/1977 | Simmons | Plt. 34 |
| P.P. 4,793 | 11/1981 | Simmons | Plt. 34 |

OTHER PUBLICATIONS

Childers, N. F. from Chapter II: "Apple Regions, Production, and Varieties", *Modern Fruit Science* (4th Ed., 1969), Rutgers Univ., pp. 22–29.

*Primary Examiner*—James R. Feyrer
*Attorney, Agent, or Firm*—Eugene D. Farley

[57] ABSTRACT

The new and distinct variety of apple tree is a mutation of the Law strain of Red Rome Beauty Apple (U.S. Plant Pat. No. 1,550). The new variety of apple tree is characterized by: The tendency for a high percentage of the leaf axillary buds to develop into spurs and/or shoots; the tendency for the purse to become enlarged during fruiting; the tendency to produce uniformly large fruit; and improved fruit color characteristics.

3 Drawing Sheets

The present invention relates to a new and distinct variety of apple tree which was discovered by me as a limb sport of the Law strain of Red Rome Beauty (U.S. Plant Pat. No. 1,550) in my cultivated orchard on my ranch near Brewster, Wash.

The new variety came to my attention because of its uniquely significant novel characteristics, as follows:

1. The tendency for a high percentage of the leaf axillary buds to develop into spurs and/or shoots.
2. The tendency for the purse to become enlarged during the time the fruit is on the spur.
3. The tendency to bear uniformly large fruit, particularly as contrasted to the fruit of other spur Rome Beauty cultivars which tend to be somewhat deficient in size.
4. The distinctly higher red coloration that covers a higher percentage of the apple surface.

Considering these in further detail:

Rome Beauty cultivars tend to have a large percentage of the leaf axillary buds that remain dormant. This is particularly true of buds on the more vigorous shoots (shoots that grow more than 15 to 18 inches in one year). Normally, if a shoot grows 36 inches or more in a year, the basal 12 to 18 inches of the shoot will have a high percentage of "blind" buds. These "blind" buds are merely leaf axillary buds that fail to grow and develop during the season following the year in which they are laid down. The typical Rome Beauty tree, therefore, is characterized by rather long pieces of branch that are unbranched, unspurred and unfruitful.

From a practical standpoint the above described growth habit results in productivity levels that are lower than some other apple cultivars. In addition, the prunic methods used to compensate for this growth habit are expensive, increasing over-all production costs.

By the end of the second growing season my newly discovered apple variety, Tift Spur Rome #21, normally has in excess of 95% of the leaf axillary buds that develop into spurs or shoots. Continued study reveals that when the tree grows it is very vigorous and a high percentage of the basal axillary buds will develop into shoots and spurs during the same season that they are laid down.

Among other things, this results in, a much greater level of fruitfulness as well as in a tree that can be pruned and trained more easily. It also results in the need for more shoot removal on the lower portions of the trunk while the trees are in the nursery.

These conclusions are supported by the following data comparing growing characteristics, with special emphasis on spur density, of Tift Spur Rome #21 with five other Rome Beauty apple varieties all grown in the Western United States, specifically in southwest Washington (Tift Spur Rome #21) and southern Utah (the remaining varieties):

| | Spur Density *1 | | |
|---|---|---|---|
| Strain | Plant Pat. | Weak Shoots *2 | Vigorous Shoots *3 |
| Nero Rome | Unpatented | 6.36 *4 | 14.4 |
| Law Red Rome | 1550 | 7.08 | 15.3 |
| Law Spur Red Rome | 4096 | 8.91 lb | 27.9 b |
| Spuree Rome | 3198 | 8.28 b | 29.2 b |
| Stark Spur | 4793 | 9.06 b | 28.3 b |
| Tift Spur Rome #21 | | 8.49 b | 35.4 c |

*1: Number of spurs per square centimeter of limb cross-sectional area on unpruned limbs of vigorous growing trees.
*2: Shoots that grew 20 to 40 centimeters (cm) per season (average cross-sectional area .32 cm 2" from base).
*3: Shoots that grew 40 to 80 cm per season (average cross-sectional area .85 cm 2" from base).
*4: Means separated using Duncans multiple range test (n = 10 shoots per strain).

The above data illustrate that there is little differentiation between "spur" type strains of Rome Beauty in terms of "spur density" on weak or low vigor shoots. On strong or high vigor shoots or trees there is a difference in spur density. This difference occurs because the other strains retain the original Rome Beauty tendency, wherein a high percentage of the leaf axillary buds on the basal ⅓ to ½ of the shoot's length remains quiescent (not developing into the shoots or spurs). Tift Spur Rome #21, however, has an excess of 95 percent of these buds that will develop into spurs, shoots or branched shoots are illustrated in FIG. 1.

The practical significance of this trait is that a Tift Spur Rome #21 tree will have a greater production potential when grown under conditions that result in vigorous vegetative growth. These conditions arise commonly in high density plantings where heavy pruning is required to control inter and intra tree crowding and shading.

The second morphological characteristic that is distinctive of my newly discovered cultivar is the tendency for the purse to swell and become "fleshy" during the period of time that the fruit is attached. It is not uncommon for the purse to be ⅜ths inch in diameter and 1½ inches in length during the fruiting period. Following the removal of the fruit the purse shrinks to a more "normal" size.

This tendency of the purse to enlarge or swell whenever there is a developing fruit present is a unique characteristic among Rome Beauty apple strains. The swelling appears to derive partially from additional xylem and phloem development, but mostly from development of a core of undifferentiated cells. The physiological effect of this swelling is not known for certain. However it appears to be analogous to the swelling of the purse in De Anjou pears. In the case of the latter, it is recognized that there is a direct relationship between the degree of swelling and the fruit size.

Measurements made of fruit size during the 1989 growing season consistently showed that the fruit size of Tift Spur Rome #21 was greater on fruits borne of spurs than on terminals. The largest fruits tended to be located on the spurs with enlarged purses. This characteristic is not the result of chemical treatment, as it was observed on grafted branches that had received no spray at all.

FIG. 1 shows a length of branch after the second growing season. It was taken of a dormant shoot, so even though the purses appear large, they became significantly larger during the ensuing growing season. FIG. 1 also illustrates Tift Spur Rome #21's unique habit of growing dards (shoots 2½ to 10 cm long with a terminal flower bud), spurs and short shoots from the leaf axillary buds during the first growing season, making the limb appear to be older than it really is.

The dards and spurs tend to bloom at the beginning of the second growing season and then grow additional dards from the purse of the fruiting spur. The development of numerous and large purses accordingly contribute significantly to the production capacity of the tree.

The third characteristic that distinguishes my new cultivar is its tendency to produce large fruits, i.e. fruits having a size of 8 ozs (224 grams) or larger. This consistently larger fruit size may be a concomitant of the swollen or enlarged purse characteristic noted above. The latter characteristic may play a role in the production of larger fruit by providing a better connection between the fruit and the tree vascular system.

The consistently larger fruit size of Tift Spur Rome #21 is evidenced by the following comparative data obtained from observations made on fruits from trees of similar age, training system, pruning and crop density, with the exception that the Nero Rome trees were 28 years old while the other trees were from five to nine years old:

| Strain | Fruit Size Plant Patent | Average Diameter |
|---|---|---|
| Nero Rome | Unpatented | 6.86 cm |
| Law Red Rome | 1550 | 6.61 |
| Law Spur Red Rome | 4096 | 6.24 |
| Spuree Rome | 3198 | 6.68 |
| Stark Spur Rome | 4793 | 6.55 |
| Tift Spur Rome #21 | | 7.03 |

In this tabulation the fruits having diameters of 6.86 cm and larger are classified as large and command a premium price over the mid-size fruits (6.24 to 6.7 cm). During the 1987, 1988 and 1989 market seasons this premium amounted to from $2 to $3.50 per box. The significantly larger size of Tift Spur Rome #21 accordingly is of considerable economic advantage.

The fourth characteristic distinguishing my new cultivar is that its fruit typically has a higher red color factor than do conventional Rome Beauty applies, for example Starkspur Rome, or Lawspur Rome. The color tends to develop earlier, and to fill in more completely the areas that are in contact with the limbs, leaves or other fruits, i.e. the "blanked out" areas. This is of great significance in view of the market preference for a red coloration over the entire surface of the fruit.

Comparisons of the fruit color of the various Rome Beauty apple strains indicates:

| Strain | % 95–100 Color | % 80–95% Color | % less than 80% Color |
|---|---|---|---|
| Nero Rome | 0 | 5 | 95 |
| Law Red Rome | 28 | 30 | 42 |
| Law Spur Red Rome | 43 | 21 | 36 |
| Spuree Red Rome | 56 | 27 | 17 |
| Stark Spur Rome | 52 | 29 | 19 |
| Tift Spur Rome #21 | 61 | 26 | 13 |

All the color judgments were made on fruits at the mature ripe stage of development. This occurs for most Rome Beauty strains at approximately 155 to 160 days post bloom.

The color separations noted above were determined with a "Pennwalt Color Sorter" for the Nero, Law Red, Law Spur and Tift Rome Strains and by visual observations for the Spuree and Stark Spur strains.

The economic significance of the highly developed color of Tift Spur Rome #21 (see FIG. 3) is indicated by the fact that in the years 1988–1989 the market value of Rome Beauty Apples showing 95%–100% color was almost double that of Rome Beauty apples showing 80%–95% color. Apples showing less than 80% color routinely were diverted to processing for sauce or slices.

Foliage coloration is similar between all compared strains when grown under similar fertility, pruning, training, water and climatic conditions.

There is significant red coloration in the veins and petiole of the leaves of all strains which varies in intensity more in relation to time of growing season and temperature than with strain differences.

Internode distances vary between "non-spur" and "spur" strains, but the significant difference is that the Tift Spur Rome #21 develops more spurs, dards and shoots than the other strains.

Taste tests show little or no differentiation of the strains on the basis of flesh taste and aroma.

Asexual reproduction by grafting of my new apple variety has been performed at my orchard near Brewster, Wash. Continued observation and testing have established fully that the distinctive characteristics descirbed above are fixed, and transmitted through successive generations.

The accompanying drawings show typical specimens of the limbs and fruit of my new apple variety.

FIG. 1 illustrates a typical limb of my new apple variety Tift Spur Rome #21 illustrating the large number of axillary buds that have developed into spurs or shoots.

Figure 2:
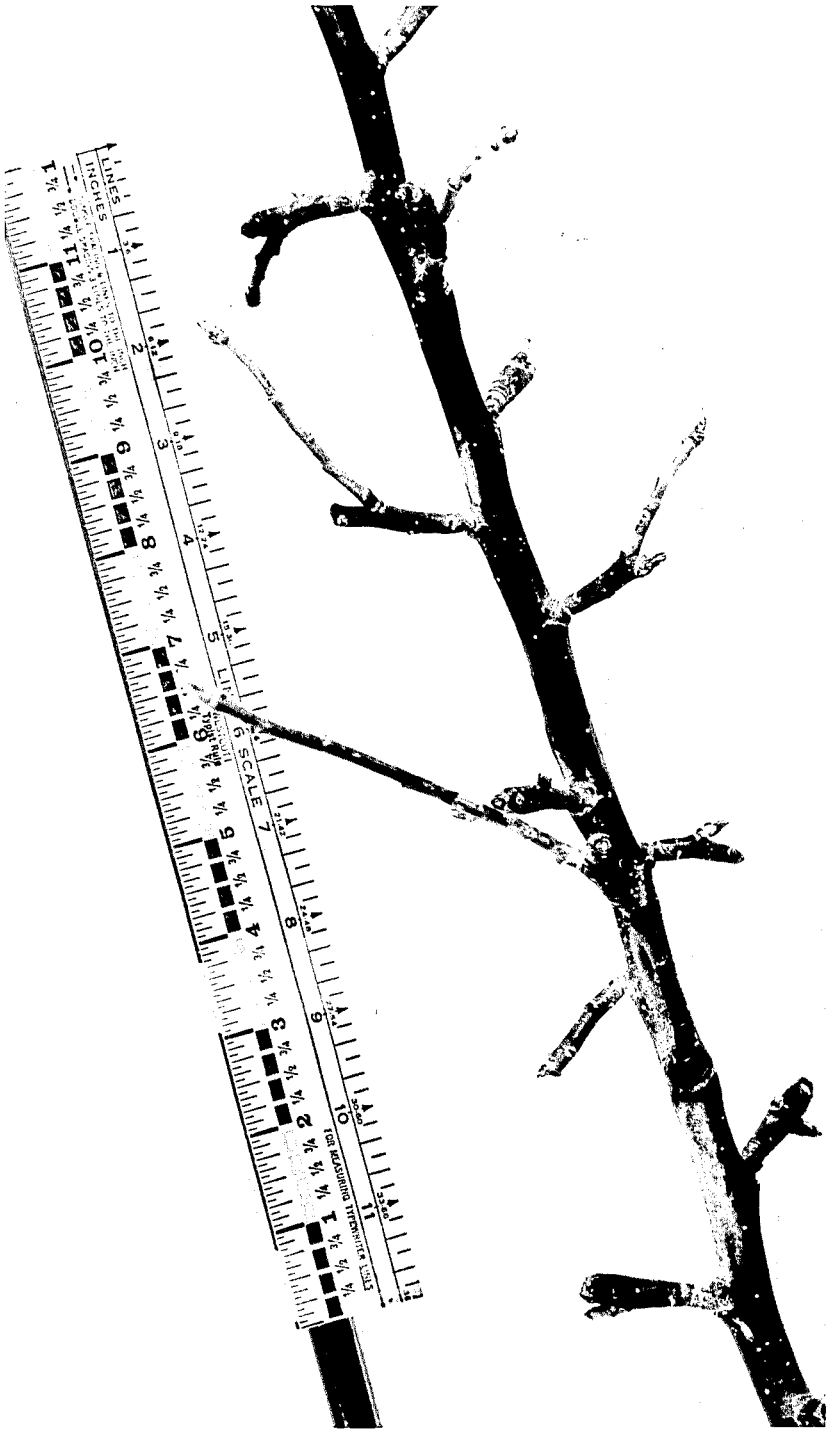

FIG. 2 is an illustration of a branch of my new apple variety illustrating the tendency for the purse to become enlarged. The purses are the heavy and enlarged formations with some leaf and fruit buds projecting from the sides and ends. On the conventional Law strains these purses generally are non existent and, when present, are much smaller.

Figure 3:
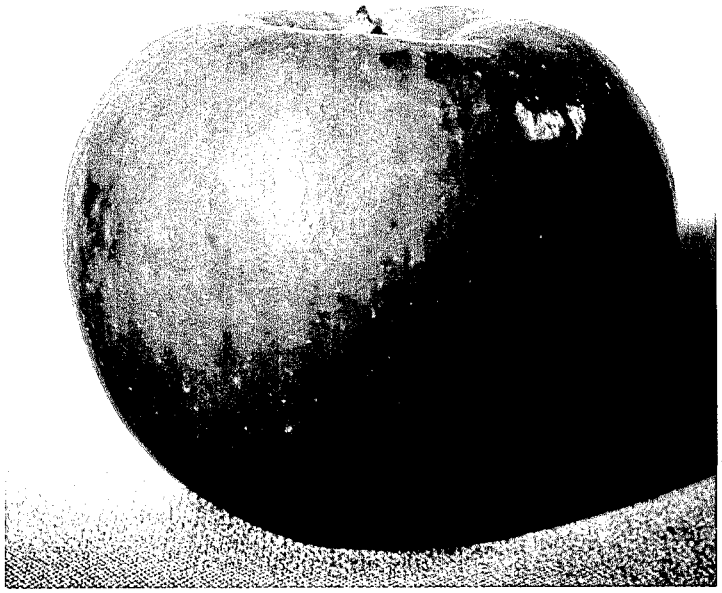

FIG. 3 is an illustration of the fruit of my new apple variety, illustrating its enhanced size and uniform deep red coloration.

The following is a detailed description of my new variety with color terminology in accordance with the Munsell Color Chart, as indicated, except where general color terms of ordinary dictionary significance are obvious:

Tree: Medium size (⅔ size of Nero Red Rome), spreading, vigorous, highly precocious, heavily spurred, annual bearer.

*Trunk.*—Stocky, smooth, moderately branched.

*Shoots.*—Vigorous, heavily spurred (95%+ of leaf axillary buds develop into spurs or shoots), light reddish brown to olive brown, lenticled prominent, white, scattered irregularly.

*Leaves.*—Dark green, smooth and waxy on top, moderately pubescent on bottom, large with moderate separation along margins, especially toward tips.

*Bearing habit.*—Elongated, profuse, enlarged spurs, tending to swell at the purse during fruiting period. Develops significantly more spurs per linear foot of one year old shoot than other Rome Beauty varieties.

Flowers: Large, white petals, stamens in single row, anthers full, yellow before shedding pollen, turning black and small after, late opening (6–10 days later than Red Delicious; same as other Rome Beauties).

Fruit: Large size, oval glossy.

*Shape.*—Oval in longitudinal section (contrasting to the more elongated shape of "Law Spur" (U.S. Plant Pat. No. 1,550). Length/Diameter ratios average 0.96 vs. 1.01 for "Law Spur".

*Cavity.*—Smooth, deep (⅜ inch), prominent, flared at apex.

*Basin.*—Wide (1–1¼ inches), deep (⅜ inch), ribbed.

*Stem.*—Elongated (normally 1½ inches long), slender, smooth.

*Calyx.*—Segments persistant, acute, separate at base, converged, heavily pubescent.

*Skin.*—Smooth, glossy, waxy finish, lenticels (dots) scattered and obscure, lenticels slightly sunken, abundant toward shoulder.

*Color.*—Bright red, almost entire surface colored including basin and cavity, rated "Strong Red", Hue 5 R 4/12 on the Munsell Color Chart.

*Finish.*—Wax bloom lacking, scarfskin lacking, wax smooth, slightly oily particularly following storage.

*Flesh.*—White, hard, crisp, juicy.

*Flavor.*—Sweet, slightly acid, distinct, lacks aroma.

*Seeds.*—Brown to dark brown, 4 to 6, large, elongated, sharp at embryo end, rounded distally.

*Bundles.*—Inconspicuous, clear, lacking chlorophyll, single row, symmetrically placed, fused toward calyx (closed calyx).

*Storeability.*—Store well in regular, cold or C.A. storage, retains quality, non yellowing flesh.

Use: Excellent for cooking and processing.

I claim:

1. A new and distinct variety of Rome Beauty apple tree, substantially as herein shown and described, characterized particularly by the tendency for a high percentage of leaf axillary buds to develop into spurs and/or shoots; the tendency for the purse to become enlarged during the time the fruit is on the spurs; the tendency to bear uniformly large fruit; and the tendency to bear fruit of higher red color factor and covering a higher percentage of the fruit surface than is characteristic of conventional Rome Beauty Apples.

* * * * *